(12) United States Patent
Carragher et al.

(10) Patent No.: US 9,594,008 B2
(45) Date of Patent: Mar. 14, 2017

(54) PREPARATION OF SPECIMEN ARRAYS ON AN EM GRID

(71) Applicants: THE SCRIPPS RESEARCH INSTITUTE, La Jolla, CA (US); Bridget Carragher, San Diego, CA (US); Clinton S. Potter, San Diego, CA (US); Tilak Jain, Encinitas, CA (US)

(72) Inventors: Bridget Carragher, San Diego, CA (US); Clinton S. Potter, San Diego, CA (US); Tilak Jain, Encinitas, CA (US)

(73) Assignee: The Scripps Research Institute, La Jolla, CA (US)

( * ) Notice: Subject to any disclaimer, the term of this patent is extended or adjusted under 35 U.S.C. 154(b) by 41 days.

(21) Appl. No.: 14/372,274

(22) PCT Filed: Jan. 14, 2013

(86) PCT No.: PCT/US2013/000018
§ 371 (c)(1),
(2) Date: Jul. 15, 2014

(87) PCT Pub. No.: WO2013/109405
PCT Pub. Date: Jul. 25, 2013

(65) Prior Publication Data
US 2015/0090899 A1    Apr. 2, 2015

Related U.S. Application Data

(60) Provisional application No. 61/632,046, filed on Jan. 17, 2012.

(51) Int. Cl.
*G01N 1/28* (2006.01)
*G01N 1/30* (2006.01)
(Continued)

(52) U.S. Cl.
CPC ............. *G01N 1/28* (2013.01); *G01N 1/30* (2013.01); *G01N 1/31* (2013.01); *H01J 37/20* (2013.01);
(Continued)

(58) Field of Classification Search
CPC .... G01N 1/28; G01N 1/30; G01N 1/31; H01J 37/20; H01J 37/261; H01J 2237/20;
(Continued)

(56) References Cited

U.S. PATENT DOCUMENTS 3,768,914 A * 10/1973 Kinney .................... G01N 1/31
356/244
6,063,339 A * 5/2000 Tisone ................. B01J 19/0046
422/509

(Continued)

FOREIGN PATENT DOCUMENTS

JP    2000195455 A *  7/2000

OTHER PUBLICATIONS https://www.tedpella.com/grids_html/gilder.htm, copyright 1996.*
(Continued)

*Primary Examiner* — Wyatt Stoffa
(74) *Attorney, Agent, or Firm* — Hugh Wang; Thomas Fitting; Mike Whittaker

(57) ABSTRACT

The invention provides methods and compositions for preparation of complex specimen arrays for analysis by electron microscopy. These methods and compositions can permit high throughput screening of samples on single EM grid supports using sample volumes in the nanoliter and picoliter range.

19 Claims, 3 Drawing Sheets

(51) Int. Cl.
*G01N 1/31* (2006.01)
*H01J 37/20* (2006.01)
*H01J 37/26* (2006.01)

(52) U.S. Cl.
CPC ......... *H01J 37/261* (2013.01); *H01J 2237/20* (2013.01); *H01J 2237/204* (2013.01); *H01J 2237/2007* (2013.01); *H01J 2237/208* (2013.01); *H01J 2237/2602* (2013.01)

(58) Field of Classification Search
CPC ......... H01J 2237/2007; H01J 2237/208; H01J 2237/2602
See application file for complete search history.

(56) References Cited

U.S. PATENT DOCUMENTS

| | | | | |
|---|---|---|---|---|
| 7,754,439 | B2* | 7/2010 | Moore | B01J 19/0046 435/287.1 |
| 2005/0107917 | A1* | 5/2005 | Smith | B25J 15/0253 700/245 |
| 2005/0232823 | A1* | 10/2005 | Brock | B01L 3/0268 73/863.23 |
| 2010/0086573 | A1* | 4/2010 | Anderson | A61K 8/14 424/401 |
| 2010/0112658 | A1* | 5/2010 | Hughes | C12N 1/18 435/161 |
| 2010/0172831 | A1* | 7/2010 | Mason | A61K 9/5184 424/1.29 |
| 2010/0181495 | A1* | 7/2010 | Lihl | G01N 1/42 250/442.11 |
| 2010/0240870 | A1* | 9/2010 | Su | G01N 33/54346 530/363 |
| 2011/0192987 | A1* | 8/2011 | Qian | G21K 1/025 250/440.11 |
| 2011/0313113 | A1* | 12/2011 | Sakamoto | C08F 2/10 525/384 |
| 2012/0241607 | A1* | 9/2012 | Bose | H01J 37/20 250/307 |
| 2013/0337066 | A1* | 12/2013 | Zhang | A61K 39/0011 424/489 |

OTHER PUBLICATIONS

Booth DS, et al., "Visualizing Proteins and Macromolecular Complexes by Negative Stain EM: from Grid Preparation to Image Acquisition." Journal of Visualized Experiments : JoVE. 2011;(58):3227. doi:10.3791/3227.*

Gilder Grids, https://www.tedpella.com/grids_html/gilder.htm, copyright 1996.*

Barbulovic-Nad, Irene., et al., "Bio-Microarray Fabrication Techniques—A Review," Critical Reviews in Biotechnology, 26:4, 237-259 (2006).*

* cited by examiner

PREPARATION OF SPECIMEN ARRAYS ON AN EM GRID

BACKGROUND OF THE INVENTION

The following discussion of the background of the invention is merely provided to aid the reader in understanding the invention and is not admitted to describe or constitute prior art to the present invention.

Screening of samples using transmission electron microscopy (EM) is often used in to characterize proteins such as antibodies used for therapeutics, viruses or virus like particles used in vaccines, drug delivery particles, or other formulations of nanoparticles. Screening may also be used to determine optimal conditions for 2D and 3D crystallization of proteins, optimizing preparation conditions for a novel protein or other macromolecular complexes, as well as formulation optimization.

EM applications such as those discussed above often require the analysis of a large number of conditions in parallel. EM sample preparation typically requires a cumbersome procedure of obtaining several negative stained samples on EM grid supports for each condition. EM grids typically comprise of a 3 mm diameter copper mesh (~25 µm thick) with open square windows (30 to 200 µm wide) acting as the base substrate. A thin (typically 5-50 nm) carbon film is layered on top this substrate, creating electron transparent (carbon film) regions in the open windows. Other EM grid substrate materials are usually made of other metals or semiconductor materials such as silicon, with films made of Silicon Nitride, Silicon Dioxide or Silicon Carbide. By way of example, each condition being analyzed can require (i) plasma treating one or more grids to create a hydrophilic specimen surface, (ii) pipetting 2-3 µL of the appropriate sample in an appropriate buffer onto the specimen surface, (iii) blotting the grid using filter paper to remove excess sample, (iv) pipetting 2-3 µL of stain immediately onto the specimen surface to avoid sample drying, (v) blotting the grid again using filter paper to remove excess stain, and (vi) allowing the stain to dry. In many cases staining using this process requires optimization of several conditions, such as concentration (sample and stain), buffer constituents, pH, sample and stain application time. This results in a large number of grid trials, which entail loading individual grids into the electron microscope for analysis of each condition, and wastes large volumes of what are often very precious sample material.

BRIEF SUMMARY OF THE INVENTION

It is an object of the invention to provide methods and compositions preparation of complex specimen arrays for analysis by electron microscopy. These methods and compositions can permit high throughput screening of samples on single EM grid supports using sample volumes in the nanoliter and picoliter range (required for rare and difficult to obtain samples). Because picoliter scale volumes will not cover an entire EM sample grid surface under achievable contact angles, each EM sample grid may be processed to provide an array of specimen locations on a single grid.

In a first aspect, the present invention provides methods for preparing an electron microscopy sample on an EM sample grid. The methods comprise:

a. dispensing a plurality of discrete specimens onto an EM sample grid in an ordered array of specimen locations, each specimen of the plurality of discrete specimens being placed into an individual specimen location in the array of locations, and each individual specimen location in the array of locations having an area of between about 2000 $\mu m^2$ to about 70,000 $\mu m^2$ (for example, each location is a circular spot of between about 50 µm and about 300 µm in diameter); and b. applying a discrete volume of a stain material suitable for contrast enhancement in an electron microscope to each individual specimen location in the array of locations that received a specimen.

In certain embodiments, a wash step precedes the application of stain to the specimen locations. In preferred embodiments, excess wash material is removed with a porous or bibulous material, or microstructures that induce local capillary effects, that "blots" or "wicks" material away from the specimen location. By way of example such a method may comprise:

a. dispensing a plurality of discrete specimens onto an EM sample grid in an ordered array of specimen locations, each specimen of the plurality of discrete specimens being placed into an individual specimen location in the array of locations, and each individual specimen location in the array of locations having an area of between about 2000 $\mu m^2$ to about 70,000 $\mu m^2$ (for example, each location is a circular spot of between about 50 µm and about 300 µm in diameter);

b. applying a discrete volume of a wash solution to each individual specimen location in the array of locations that received a specimen, and removing excess wash solution by contact with a bibulous or porous material at the periphery of each individual specimen location in the array of locations; and c. applying a discrete volume of a stain material suitable for contrast enhancement in an electron microscope to each individual specimen location in the array of locations that received a specimen.

Suitable stains for use in the present methods include ammonium molybdate, uranyl acetate, uranyl formate, phosphotungstic acid, osmium tetroxide, osmium ferricyanide and auroglucothionate, commercially available stains such as NANOVAN™ Methylamine Vanadate (Nanoprobes, Inc.) and NANO-W™ Methylamine Tungstate (Nanoprobes, Inc.) as well as other stains that are described in the general literature.

Creation of the blotting regions on the grids can be performed by a variety of fabrication techniques. The material used as the blotting material can be patterned by microfabrication techniques on the grid. By way of example only, thin film blotting material (such as dried gels, adsorption papers and porous membranes) can be laser machined and then adhered to the surface of a grid. In another example, the blotting material in liquid form can be printed using inkjet printing or stamped using soft-contact lithography, and then desiccated. Other methods can include creating nano-wires and polymer-matrixes by first forming a patterned seed layer and subsequent deposition/polymerization. This list is not meant to be limiting.

In various embodiments, the sample volume(s) are applied to subregions of the EM sample grid surface by spotting such as by the use of robotic micropipetting techniques, or more preferably using "ink jet" printing technologies. Ink jet printing technologies known in the art include devices equipped with pins, or sample ejection elements that dispense using thermal, sonic, or piezoelectric impulses. Among the methods mentioned above, the inkjet method is a preferred sample application method because of its ability to carry out high-density, precise spotting. As used herein, the term "picoliter volumes" refers to a volume of liquid that is at least 1 pL and which is less than 1 nL; "nanoliter volumes" refers to a volume of liquid that is at least 1 nL and which is less than 1 µL; and "microliter volumes" refers to a volume of liquid that is at least 1 µL and which is less than 1 mL.

The inkjet method is a method in which a solution of interest is placed in an extra-fine nozzle, pressure or heat is instantaneously applied on a portion near the nozzle's tip to correctly eject an extremely low volume of aqueous material from the nozzle's tip and directed to the surface of the EM grid. For example, the inkjet head may be a bubble-jet head having a mechanism for discharging a solvent with the application of thermal energy; a piezo-jet head that ejects a solution using a piezoelectric element; etc. Preferably, the drop dispenser comprises multiple nozzles that can be used to "print" sample volumes, wash solutions, stains, etc., onto the discretely addressable sample locations of the EM sample grid. When the aqueous solution is ejected from the inkjet head, each droplet forms a circular spot, the thickness and expansion of which is controlled by the structure of the EM grid surface. Connection with an adjacent spot can be effectively prevented even when the spots of sample solution are spotted in high density. On a standard ~3 mm diameter EM grid (2 mm diameter imaging area), when the dispensed spots are 50-300 µm in diameter, transfer of the entire contents of the 12, 24, 48, 96 or 384 well-plate is possible.

In a related aspect, the present invention relates to EM specimen grids that are configured for use in the present invention. The EM specimen grids comprise a plurality of discrete specimen locations delimited from one another by peripheral regions comprising a bibulous or porous material, or microstructures that induce local capillary effects, that "blots" or "wicks" material. These grids are referred to herein as "blotting microwell array" or "BMA" grids.

In another related aspect, the present invention relates to a system for dispensing aqueous materials onto an EM sample grid at individual specimen locations in an ordered array of specimen locations, each individual specimen location in the array of locations having an area of between about 2000 µm$^2$ to about 70,000 µm$^2$. The systems comprise:

a. a holder for reversibly receiving an EM sample grid;

b. a picoliter to nanoliter volume drop dispenser (e.g., an inkjet printing element) configured to dispense fluid from one or more dispensing elements onto each individual specimen location in the array of locations;

c. a drive mechanism to position the EM sample grid relative to the one or more dispensing elements; and d. one or more reservoirs operably linked to the drop dispenser for holding one or more aqueous solutions to be dispensed onto each individual specimen location in the array of locations.

The present invention is particularly applicable to transmission electron microscopy. Transmission electron microscopy (TEM) is a microscopy technique whereby a beam of electrons is transmitted through an ultra thin specimen, interacting with the specimen as it passes through. An image is formed from the interaction of the electrons transmitted through the specimen; the image is magnified and focused onto an imaging device, such as a fluorescent screen, on a layer of photographic film, or to be detected by a sensor such as a CCD camera. The image is in effect assumed to be a simple two-dimensional projection of the sample down the optical axis.

The methods and compositions of the present invention may be used to analyze particles selected from the group consisting of polymer beads, metal beads, proteins, protein-metal bead complexes, protein-polymer bead complexes, viruses, virus-like particles, liposomes and other nanoparticles. The methods may also be used to analyze sub micron aggregates of these particles.

DETAILED DESCRIPTION OF THE INVENTION

Molecular microscopy is a non-invasive molecular imaging technology that uses advanced specimen preparation and imaging methods designed specifically to visualize complex biological samples, under conditions close to their native state. For well-ordered samples such as viruses, and virus-antibody complexes, the achievable resolution can be <0.4 nm. High-throughput molecular microscopy combines robotic instruments, automated data collection and processing software, and a relational database into a pipeline to prepare, image, and analyze samples in a reproducible manner and with throughputs capable of addressing biopharmaceutical characterization needs in a statistically significant manner. Samples are preserved in solution by vitrification (using an automated cryogenic robot) or by negative stain, and then imaged using a transmission electron microscope (TEM) controlled by automated software that enables sampling of a significant portion of the specimen. Data is analyzed and stored in a secure database that tracks all aspects of sample preparation, imaging, and analysis to provide our current customers with a tightly controlled system for biological imaging.

In electron microscopy, staining is usually done with heavy metal salts commonly derived from molybdenum, uranium, or tungsten. Heavy ions are used since they will readily interact with the electron beam and produce amplitude contrast. A small drop of the sample is deposited on the carbon coated grid, allowed to settle for approximately one minute, blotted dry if necessary, and then covered with a small drop of the stain (for example 2% uranyl acetate). After a few seconds, this drop is also blotted dry, and the sample is ready to be imaged in the TEM.

Figure 1:
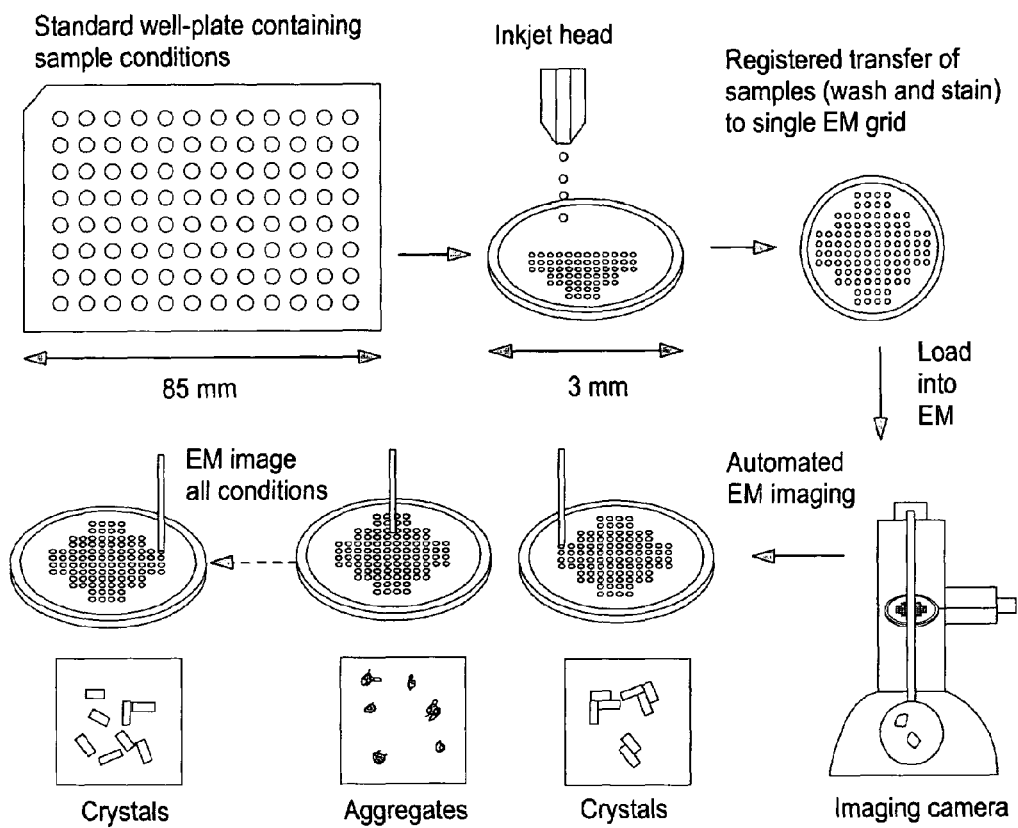
FIG. 1 depicts in schematic form an exemplary method for conducting a high-throughput screen of samples on an EM compatible grid according to the invention.

The present invention here describes methods and compositions for conducting a high-throughput screen of samples on a single EM compatible grid. As shown in FIG. 1, a standard well-plate (96 or 384 wells) contains the sample conditions to be tested (in lower throughput screens 12, 24 and 48 well-plates can also be accommodated). An inkjet head capable of delivering samples (picoliters to microliters) transfers the sample conditions from the stock plate onto a targeted area of a single EM grid. The dispensed samples are registered precisely for downstream identification and tracking during EM imaging at low and high magnification. Multiple inkjet heads can be used to facilitate sample dispensing onto the EM grid. On a 3 mm diameter grid (2 mm imaging area), when the dispensed spots are 50-300 µm in diameter, transfer of the entire contents of the 12, 24, 48, 96 or 384 well-plate is possible. This allows for complete mapping of sample conditions from the standard well-plate onto the grid. For screens requiring more thousands of sample conditions, only a few EM grids will be required.

Figure 2:
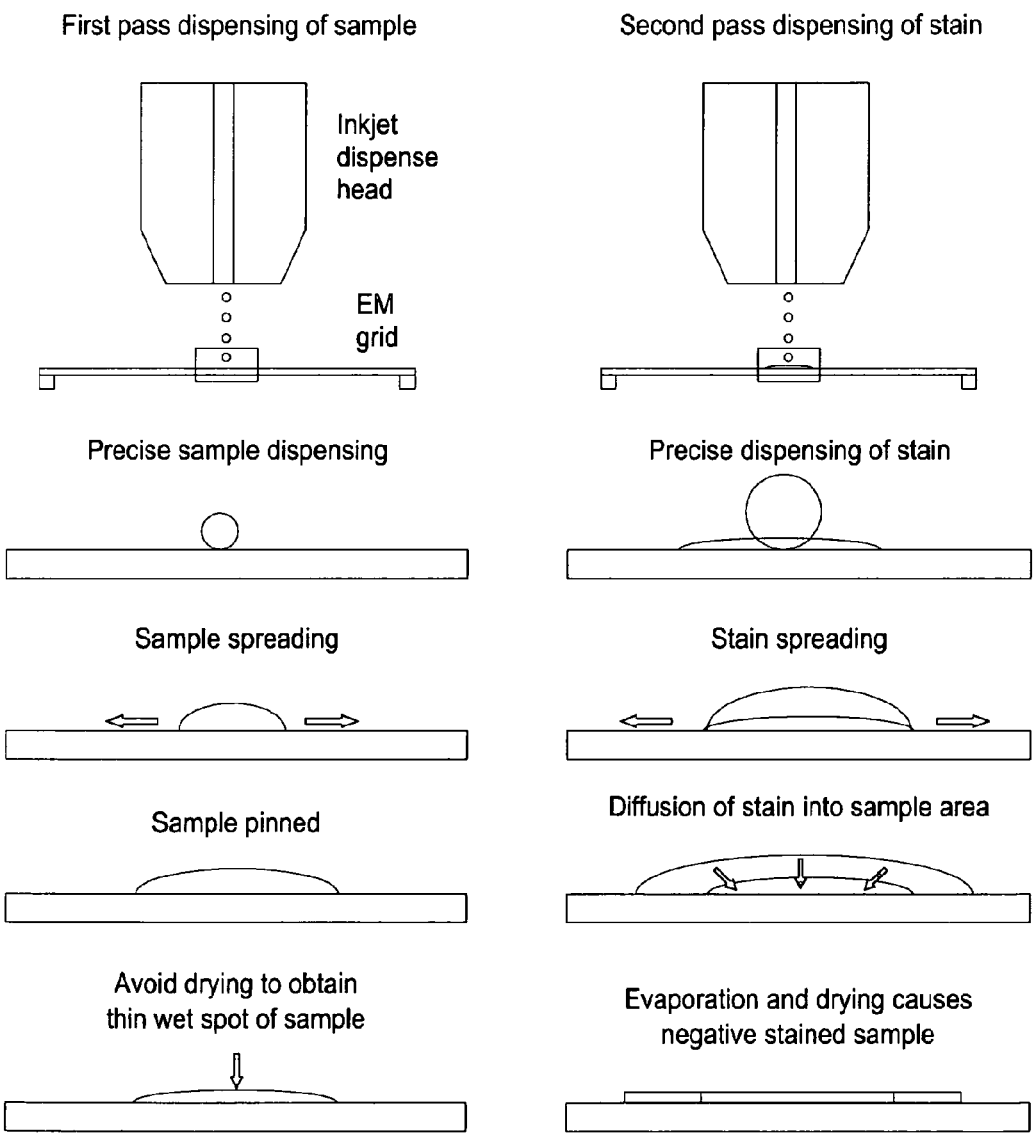
FIG. 2 depicts in schematic form an exemplary method for dispensing of samples and stain on an EM compatible grid according to the invention.

In one scenario of the invention, the samples are dispensed and dried on the grid prior to any staining. This scenario can be used if the samples are relatively stable and the drying (accompanied by phenomenon such as salt crystallization) does not lead to particle destabilization or staining failure. In such situations, once inkjet sample transfer is complete, the grid can be washed and flooded with stain (3 μL). Alternatively, the stain can be dispensed onto the individual sample spots on the grid using a single inkjet head that precisely targets the registered areas. As shown in FIG. 2, if multiple heads are used, the dispensing of stain can take place before the dispensed sample dries. In either case, dispensing of stain using an inkjet head allows for much greater control of volume and uniformity of spreading across the grid, which is not possible with the standard blotting process. Additionally, multiple staining conditions (concentration and type of stain) can be tested on similar sample conditions. Multiplexing at the grid level allows only a single grid (or a few, compared to hundreds to thousands) to be loaded in the electron microscope for the screen.

Sample constituents can include dissolvable materials such as sugars, gels and buffer salts that prevent the destabilization of sensitive samples during the brief period of evaporation after the first droplet lands and spreads on the grid. As shown in FIG. 2, diffusion of the stain particles occurs after the second droplet lands on the sample spot. Along with the spatial precision of droplet transfer, the time interval between the first and second droplet can also be accurately controlled within a few hundred milliseconds to seconds. Multiple dispense heads can allow for intermediate washes, bindings and reactions, between the sample and stain droplet. The surface properties of the grid (flatness, wetability and atomic roughness) govern the spreading of droplets given comparable environmental conditions. The grid surface can be made hydrophilic (or super-hydrophilic) to ensure rapid spreading of the droplets and faster diffusion between the sample and stain.

Figure 3:
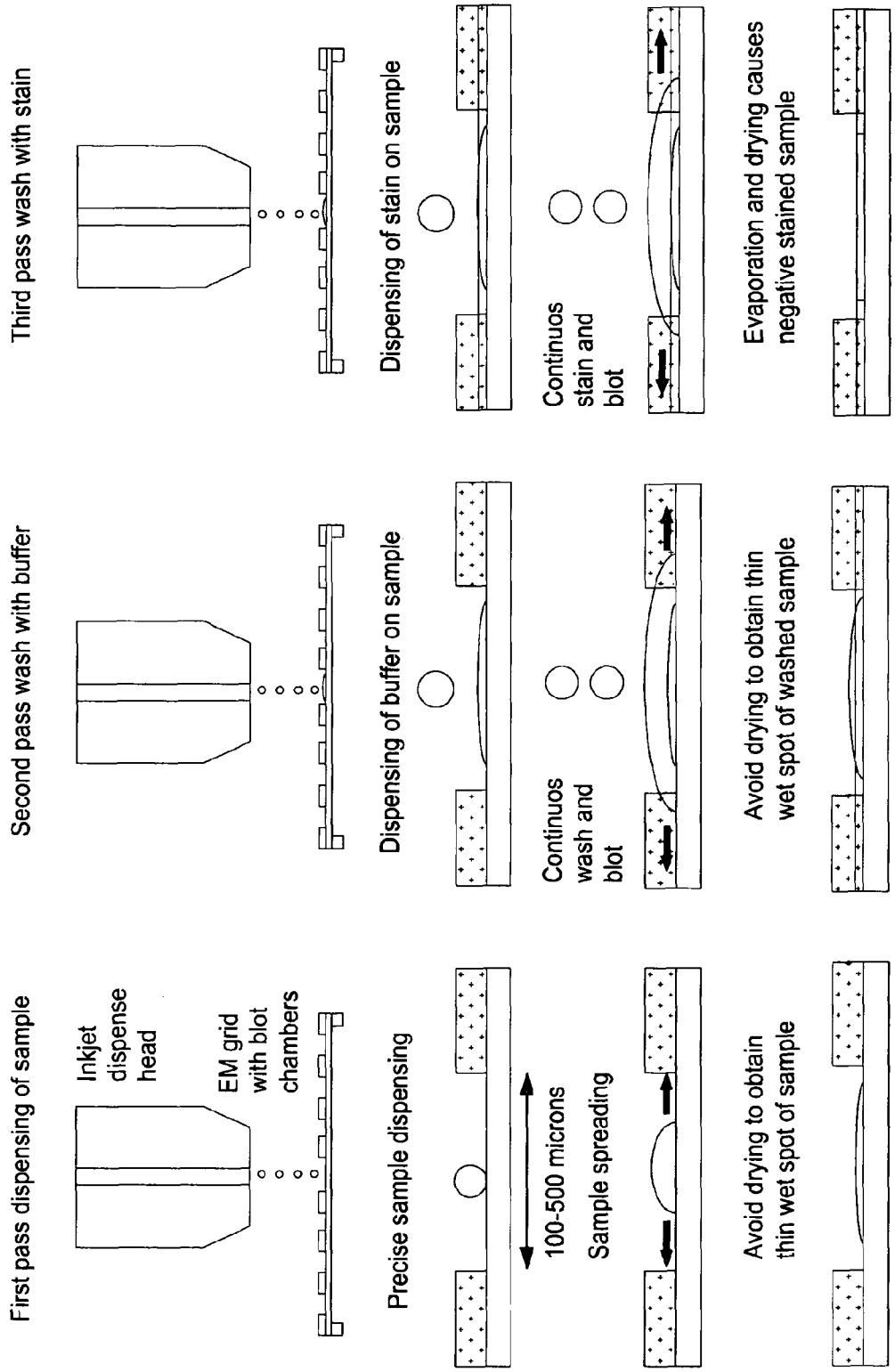
FIG. 3 depicts in schematic form an exemplary method for dispensing of samples and stain on an EM compatible grid that comprises an array of blotting material surrounding the targeted area on the grid according to the invention.

To further control sample washing and staining without significant evaporation prior to drying, an array of blotting material can surround the targeted area on the grid as shown in FIG. 3. After sample spotting, the wash and stain steps with larger dispense volume leads to local blotting in the surrounding material. In this manner the samples can be washed, without significant buildup in the target area. Similarly, the subsequent dispensed stain will be blotted locally to create an even layer of negatively stained sample. As noted above, the material used as the blotting material can be patterned by microfabrication techniques on the grid. In one method, thin film blotting material (such as dried gels, adsorption papers or porous membranes) can be laser machined and then adhered to the surface of a grid. In another method, the blotting material in liquid form can be printed using inkjet printing or stamped using soft-contact lithography, and then desiccated. Other methods can include creating nano-wires and polymer-matrixes by first forming a patterned seed layer and subsequent deposition/polymerization. Other methods can include creating microstructures, surrounding the targeted areas that induce local capillary effects, such as an overhanging ledge or spiral with spaces of 0.5 to 10 μm between hydrophilic walls. The BMA grids can be aligned accurately with the inkjet printer to dispense the droplets between the blotting areas. The blotting areas themselves can be used as physical markers for identifying the registered samples and for downstream image recognition and processing.

While the invention has been described and exemplified in sufficient detail for those skilled in this art to make and use it, various alternatives, modifications, and improvements should be apparent without departing from the spirit and scope of the invention. The examples provided herein are representative of preferred embodiments, are exemplary, and are not intended as limitations on the scope of the invention. Modifications therein and other uses will occur to those skilled in the art. These modifications are encompassed within the spirit of the invention and are defined by the scope of the claims.

It will be readily apparent to a person skilled in the art that varying substitutions and modifications may be made to the invention disclosed herein without departing from the scope and spirit of the invention.

All patents and publications mentioned in the specification are indicative of the levels of those of ordinary skill in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations that is not specifically disclosed herein. Thus, for example, in each instance herein any of the terms "comprising," "consisting essentially of" and "consisting of" may be replaced with either of the other two terms. The terms and expressions that have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

Other embodiments are set forth within the following claims.

We claim:

1. A method for preparing an electron microscopy sample on an EM sample grid, comprising:
   discretely dispensing a plurality of specimens onto an EM sample grid to thereby provide an ordered array of discrete specimen locations, each specimen of the plurality of specimens being placed into an individual specimen location in the array of locations, and each individual specimen location in the array of locations having an area of between about 2000 $\mu m^2$ to about 70,000 $\mu m^2$; and
   discretely applying a volume of a stain material suitable for contrast enhancement in an electron microscope to each individual specimen location in the array of locations that received a specimen.

2. A method according to claim 1, wherein said specimens are dispensed by discretely applying more than one fluid to each discrete specimen location, wherein each specimen is formed by mixing the more than one fluid at each discrete specimen location.

3. A method according to one of claim 1 or 2, wherein the stain material is selected from the group consisting of ammonium molybdate, uranyl acetate, uranyl formate, phosphotungstic acid, osmium tetroxide, osmium ferricyanide and auroglucothionate.

4. A method according to one of claim 1 or 2, wherein each discrete specimen location is delimited from one another by peripheral regions comprising a bibulous or porous material, wherein the bibulous or porous material is a microfabricated material applied to the surface of the EM sample grid, wherein the microfabricated material comprises a pattern of openings in the bibulous or porous material corresponding to the ordered array of discrete specimen locations.

5. A method according to claim 4, wherein the bibulous or porous material comprises a dried gel material.

6. A method according to claim 4, wherein the bibulous or porous material comprises a fibrous material.

7. A method according to claim 4, wherein the bibulous or porous material comprises a matrix forming one or more capillary spaces.

8. A method for preparing an electron microscopy sample on an EM sample grid, comprising:
   discretely dispensing a plurality of specimens onto an EM sample grid to thereby provide an ordered array of discrete specimen locations, each specimen of the plurality of specimens being placed into an individual specimen location in the array of locations, and each individual specimen location in the array of locations having an area of between about 2000 $\mu m^2$ to about 70,000 $\mu m^2$;
   discretely applying a volume of a wash solution to each individual specimen location in the array of discrete specimen locations, and removing excess wash solution by contact with a bibulous or porous material at the periphery of each individual specimen location in the array of discrete specimen locations; and
   discretely applying a volume of a stain material suitable for contrast enhancement in an electron microscope to each discrete specimen location in the array of discrete specimen locations.

9. A method according to claim 8, wherein said specimens are dispensed by discretely applying more than one fluid to each discrete specimen location, wherein each specimen is formed by mixing the more than one fluid at each discrete specimen location.

10. A method according to claim 8, wherein the stain material is selected from the group consisting of ammonium molybdate, uranyl acetate, uranyl formate, phosphotungstic acid, osmium tetroxide, osmium ferricyanide and auroglucothionate.

11. A method according to claim 8, wherein excess wash solution is removed by discretely contacting a bibulous or porous material to the periphery of each individual specimen location in the array of discrete specimen locations.

12. A method according to claim 9, wherein the bibulous or porous material comprises a dried gel material.

13. A method according to claim 9, wherein the bibulous or porous material comprises a fibrous material.

14. A method according to claim 9, wherein the bibulous or porous material comprises a matrix forming one or more capillary spaces.

15. An EM specimen grid, comprising:
   a plurality of discrete specimen locations, each completely delimited from one another by peripheral regions comprising a bibulous or porous material, wherein the plurality of discrete specimen locations form an array of locations on the grid, each individual specimen location in the array of discrete specimen locations having an area of between about 2000 $\mu m^2$ to about 70,000 $\mu m^2$.

16. An EM specimen grid according to claim 15, wherein the bibulous or porous material comprises a dried gel material.

17. An EM specimen grid according to claim 15, wherein the bibulous or porous material comprises a fibrous material.

18. An EM specimen grid according to claim 15, wherein the bibulous or porous material comprises a matrix forming one or more capillary spaces.

19. A system for dispensing aqueous materials onto an EM sample grid at individual specimen locations in an ordered array of locations, each individual location in the array of locations having an area of between about 2000 $\mu m^2$ to about 70,000 $\mu m^2$, the system comprising:
   a holder for reversibly receiving an EM sample grid;
   a volume drop dispenser configured to discretely dispense fluid from one or more dispensing elements onto each individual location in the array of locations to thereby provide an ordered array of discrete specimen locations, at least one dispensing element in the volume drop dispenser configured to dispense picoliter volumes;
   a drive mechanism to position the EM sample grid relative to the one or more dispensing elements; and
   one or more reservoirs operably linked to the drop dispenser for holding one or more aqueous solutions to be discretely dispensed onto each individual location in the array of locations.

\* \* \* \* \*